(12) United States Patent
Wu et al.

(10) Patent No.: US 9,422,330 B2
(45) Date of Patent: Aug. 23, 2016

(54) PREPARATIVE RP-HPLC METHOD FOR PURIFYING PEPTIDES

(75) Inventors: Xiaoyan Wu, Vaerloese (DK); Are Bogsnes, Nivaa (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/580,204

(22) PCT Filed: Mar. 1, 2011

(86) PCT No.: PCT/EP2011/052964
§ 371 (c)(1),
(2), (4) Date: Sep. 4, 2012

(87) PCT Pub. No.: WO2011/107447
PCT Pub. Date: Sep. 9, 2011

(65) Prior Publication Data
US 2012/0322976 A1    Dec. 20, 2012

Related U.S. Application Data

(60) Provisional application No. 61/309,642, filed on Mar. 2, 2010.

(30) Foreign Application Priority Data

Mar. 1, 2010  (EP) ................................ 10155023

(51) Int. Cl.
*C07K 1/20* (2006.01)

(52) U.S. Cl.
CPC ....................... *C07K 1/20* (2013.01)

(58) Field of Classification Search
None
See application file for complete search history.

(56) References Cited

U.S. PATENT DOCUMENTS

| | | |
|---|---|---|
| 5,245,008 A | 9/1993 | Dickhardt et al. |
| 2006/0211616 A1* | 9/2006 | Staby et al. .................. 514/12 |
| 2009/0036652 A1 | 2/2009 | Rasmussen et al. |

FOREIGN PATENT DOCUMENTS

| | | |
|---|---|---|
| CN | 1839155 A | 9/2006 |
| JP | H04230699 A | 8/1992 |
| WO | WO 9808871 A1 * | 3/1998 |
| WO | 2005/019262 A1 | 3/2005 |
| WO | 2007/071767 A1 | 6/2007 |

OTHER PUBLICATIONS

"HPLC of Peptides and Proteins: Methods and Protocols", vol. 251, edited by Aguilar, Humana Press, Inc. (2004).*
Baczek et al., "pH Gradient Reversed-Phase Liquid Chromatography as a Fractionation Tool for the Separation of Peptides", Talanta, 2008, vol. 75, pp. 76-82.
Mant et al., "Preparative Reversed-Phase Liquid Chromatography of Proteins From Rabbit Skeletal Troponin, a Multi-Protein Complex", Journal of Chromatography A, 2002, vol. 972, pp. 101-114.
Kaliszan et al., "pH Gradient Reversed-Phase HPLC", Analytical Chemistry, 2004, vol. 76, pp. 749-760.
Wiczling et al., "Determination of pKa by pH Gradient Reversed-Phase HPLC", Analytical Chemistry, 2004, vol. 76, pp. 3069-3077.
Nokia, Pseudo-CR on Introduction of Extended Service Request, 3GPP TSG CT WG1 Meeting #55BIS (C1-085520) [Online], 3GPP, Oct. 10, 2008, P01-12, URL, http://www.3gpp.org/ftp/tsg_CT/WG1_mm-cc-sm_ex-CN1/TSGC1_56/Docs.
Jingyan Wang et al Biochemistry, 3rd edition, Book 1,Higher Education Press, p. 305.
Pharmacia Biotech's booklet Ion Exchange Chromatography, Principles and Methods.

* cited by examiner

*Primary Examiner* — Julie Ha
*Assistant Examiner* — Kristina M Hellman
(74) *Attorney, Agent, or Firm* — Rosemarie R. Wilk-Orescan

(57) ABSTRACT

A method for separating on a RP-HPLC system a polypeptide of interest from at least one unwanted component is described, wherein at least one of the elution steps is performed at or in close proximity to the pI value of the peptide of interest.

14 Claims, 7 Drawing Sheets

PREPARATIVE RP-HPLC METHOD FOR PURIFYING PEPTIDES

CROSS-REFERENCE TO RELATED APPLICATIONS

This application is a 35 U.S.C. §371 national stage application of International Patent Application PCT/EP2011/052964 (published as WO 2011/107447 A1), filed Mar. 1, 2011, which claimed priority of European Patent Application 10155023.4, filed Mar. 1, 2010; this application further claims priority under 35 U.S.C. §119 of U.S. Provisional Application 61/309,642, filed Mar. 2, 2010.

FIELD OF THE INVENTION

The present invention is related to a method for separating on a RP-HPLC system a polypeptide of interest from at least one unwanted component, wherein at least one of the elution steps is performed at or in close proximity to the pI value of the peptide of interest.

BACKGROUND OF THE INVENTION

For the purification (i.e. separation from impurities) and analysis of proteins and peptides (polypeptides), chromatography is a well-known and widely used method. A number of different chromatographic principles are applied, among these reversed phase high performance liquid chromatography (RP-HPLC). The RP-HPLC separation principle is based on hydrophobic association between the polypeptide solute and hydrophobic ligands on the chromatographic resin surface. RP-HPLC purification usually consists of one or more of the following sections: equilibration, loading, wash, elution, and regeneration.

Some impurities are poorly separated by traditional RP-HPLC carried out with a liquid phase having a pH lower or higher than the pI of the target molecule to be purified. Elution at pI is normally not the preferred mode of operation due to risk of uncontrolled precipitation of the product (i.e. peptide of interest). A pH gradient for separation of peptides was disclosed in ScienceDirect, Talanta 75 (2008), p. 76-82. Here a recurring pH gradient by repeating the same pH gradient from 2.5 to 10.5 was applied.

Various preparative reverse phase chromatography methods have been described. US2009036652 is related to purification of proteins using preparative reverse phase chromatography, WO2007071767 is related to purification of vitamin K-dependent polypeptides using preparative reverse phase chromatography and US20060211616 is related to purification of glucagon like peptides.

An optimized RP-HPLC purification method is however needed wherein good purification is obtained without the need for using an extensive process comprising a recurring pH gradient.

SUMMARY OF THE INVENTION

The present invention is related to a method for separating on a RP-HPLC system a polypeptide of interest from at least one unwanted component in a fluid mixture, the method comprising:
  a. Introducing to the RP-HPLC system a mixture comprising the polypeptide of interest, the mixture being dissolved in a mobile phase, wherein the mobile phase has a pH value which is at least 1 unit from the pI value of the polypeptide of interest
  b. adjusting the pH of the mobile phase to a pH value which is less than 1 unit from the pI value of the polypeptide of interest, wherein the adjustment in pH is done in a step-wise procedure or with a pH gradient
  c. eluting the polypeptide of interest to provide a purified composition thereof.

In one aspect of the invention a further step is added between step b and step c, wherein pH is again adjusted to a pH value which is at least 1 unit from the pI value of the peptide or protein to be purified, and wherein said adjustment is done in a step-wise procedure or with a pH gradient In one aspect of the invention the method comprises applying a gradient of an organic modifier simultaneously with step b to remove the unwanted impurities while retaining the target peptide on the RP-HPLC system.

DESCRIPTION OF THE INVENTION

Figure 1:
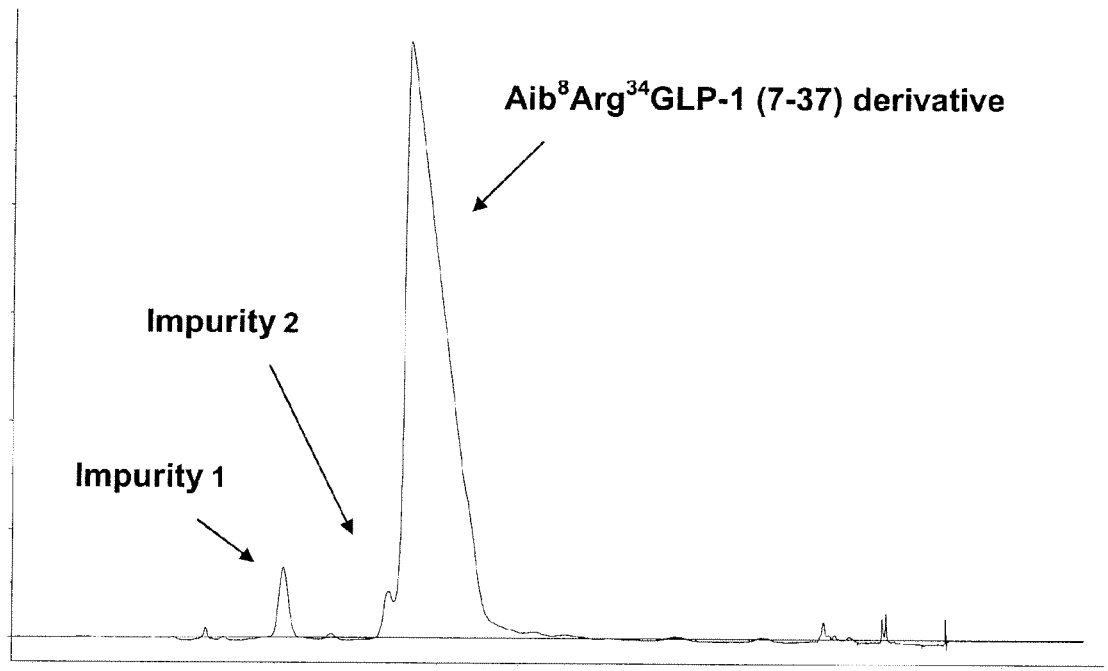
FIG. 1. Chromatogram of $AU_{280}$ versus time for the preparative separation, elution was per-formed at pH 4.5

The invention is related to a preparative RP-HPLC method for purifying polypeptides wherein at least one of the elution steps is performed at or in close proximity to the pI value of the peptide of interest.

More specifically the invention is related to a preparative RP-HPLC method for purifying a mixture comprising a polypeptide of interest, comprising the steps:
  a. Introducing to the RP-HPLC system a mixture comprising the polypeptide of interest, the mixture being dissolved in a mobile phase, wherein the mobile phase has a pH value which is at least 1 unit from the pI value of the polypeptide of interest
  b. adjusting the pH of the RP-HPLC system to a pH value which is less than 1 unit from the pI value of the polypeptide of interest, wherein the adjustment in pH is done in a step-wise procedure or with a pH gradient
  c. eluting the polypeptide of interest to provide a purified composition thereof.

In one aspect of the invention a pH gradient is used in step b to adjust the pH.

It has been found by the inventors that when applying the method of the invention a surprisingly good separation of impurities from the peptide of interest is obtained. In particular it has been possible to separate impurities which are otherwise difficult to remove by the conventional RP-HPLC methods, such as related impurities.

Also, by applying the purification method of the invention, the need for complicated purification methods for obtaining a desired separation of a polypeptide of interest from at least one unwanted component is avoided.

The term "chromatography" as used herein, refers to any technique used for the chemical separation of mixtures and components, which relies upon selective attraction among the components of a mixture for a stationary phase. Examples include adsorption chromatography, partition chromatography, ion exchange chromatography, size exclusion chromatography and affinity chromatography.

When used herein the term "RP-HPLC" means Reversed Phase High Performance Liquid Chromatography or Reversed Phase High Pressure Liquid Chromatography. HPLC is used to separate compounds based on their polarities and interactions with the column's stationary phase. Reversed-phase chromatography is an elution procedure used in liquid chromatography in which the mobile phase is significantly more polar than the stationary phase.

When used herein the term "introducing the fluid mixture" means introduction of the mixture comprising the polypeptide of interest and the at least one unwanted component to the stream of mobile phase.

When used herein the term "pI" means the isoelectric point and is the pH at which a particular molecule such as a polypeptide carries no net electrical charge.

A protein at its pI has no net charge, and the aqueous solubility is therefore at the lowest here. Hence, there is a risk of precipitation at increasing protein concentrations. At 1 pH unit above or below pI, the net charge increases significantly (depending on the amino acids involved, the net charge increases to approximately 90% of the maximum net charge), and the solubility can be assumed to be about 10 fold higher, and the protein is consequently less prone to precipitation. The general perception is that precipitation is best avoided at a pH value which is approximately 1.5-2 pH units from the pI value of a peptide or protein, where specific protein domains and other attributes may affect these values.

When used herein the term "unit" in connection with the pI value of the polypeptide of interest means the definite magnitude that is used as a standard for measurement of pH.

For example, if a polypeptide of interest has a pI value of 4.5, 1 unit from the pI value of said polypeptide is thus 3.5 or 5.5, and 1.5 units from the pI value of said polypeptide is thus 3.0 or 6.0.

When used herein the term "preparative" in connection with chromatography such as RP-HPLC, means purification by chromatography of sufficient quantities of a substance e.g. a polypeptide to be further used in the purified form. Preparative chromatography is thus opposed to analytical chromatography which is used for analysis purposes only.

In one aspect of the invention a combination of pH and an organic modifier gradient is used as a first step, and a pH gradient starting at or in close proximity to the pI value of the peptide is used as a second step in the method. According to such aspect a method is used wherein a first step comprises a pH gradient starting at a pH value which is at least 1 unit from the pI value of the polypeptide of interest and changed to a pH at or in close proximity to the pI value of said polypeptide of interest in combination with an organic modifier gradient applied until the one or more impurities which elute faster than the polypeptide of interest are eluted from the RP-HPLC system while the polypeptide of interest is retained on the system, and a second step wherein a further pH gradient is applied from a pH at or in close proximity to the pI of the polypeptide of interest and changed to a pH value which is at least 1 unit from the pI value of the polypeptide of interest. It has thus been found by the inventors that a particularly desirable purification is obtained by such combination of pH and organic modifier adjustment.

In one aspect of the invention, after the step wherein pH is at or in close proximity to the pI value of the polypeptide of interest, the pH of the mobile phase is adjusted in an additional step to at least one unit above the pI value of the polypeptide of interest. The inventors have found that the said additional step minimizes unwanted product precipitation even further.

When used herein the term "mobile phase" means the solvent which is introduced to the column.

In one aspect of the invention an isocratic elution with respect to pH and/or the concentration of the organic modifier is used in at least one elution step.

When used herein the term "isocratic elution" when used with respect to pH or the concentration of the organic modifier" means elution under conditions in which pH respectively the concentration of the organic modifier in the elution composition remains constant throughout the procedure.

In one aspect of the invention, the HPLC method is performed at 20° C. or higher. In another aspect the HPLC method is performed at an elevated temperature, i.e. a temperature above room temperature, such as between 30° C. and 70° C. In another aspect the temperature is between 40° C. and 60° C. In yet another aspect the temperature is about 50° C. In one aspect the temperature is about room temperature.

The stationary phase used for the invention may be any suitable material such as e.g. substituted siliga gel or polymeric base material. In one aspect of the invention the stationary phase is selected from the group consisting of: linear or branched alkyl chains with up to 20 carbon atoms (C20)—silica gel or phenyl— or benzene-substituted silica gel. In another aspect the stationary phase is a reverse phase (RP) gel, i.e. any stationary phase which may be eluted with an organic solvent. RP gels are known to the person skilled in the art and include e.g. Polystyrene— or Poly(divinyl) benzene silica gel. In another aspect the RP gel is an ODDMS (octadecyl-dimethylsilyl, $C_{18}$—) substituted silica gel.

The term "stationary phase" as used herein, refers to the stationary phase used in chromatography for which the mobile phase components exhibit a selective affinity. Because such affinity can take a variety of forms other than adsorption (including size exclusion or complexation), the term refers to stationary phases that adsorb the components of a fluid mixture and to stationary phases that do not technically adsorb components from the mobile phase, but which nevertheless behave as an adsorbent by slowing the migration velocity of one component relative to another in a chromatographic system. Non-limiting examples of adsorbents, i.e. chromatographic stationary phase materials, are e.g.: Substituted silica, such as C-4 silica, C-6 silica, C-12 silica, C-18 silica and phenyl-based silica, as well as polymeric materials such as polystyrene. Additional examples of chromatographic stationary phases are membranes, monolithic materials and filters.

When using a RP gel as stationary phase it may be substituted with a ligand. In one aspect the RP gel is substituted with a ligand selected from the group consisting of: $C_4$-, $C_6$-, $C_8$-, $C_{12}$-, $C_{16}$-, $C_{18}$, $C_{20}$-ligand. In one aspect the RP gel is substituted with a C18 (Octadecyl-dimethylsilyl) ligand.

When the stationary phase is a RP gel, the particles thereof may be from 2 μm to 200 μm in diameter. In one aspect of the invention the particles of the RP gel are around 15 μm in diameter. The pore size of the RP gel may be from 100 Å to 1000 Å. In one aspect the pore size of the RP gel is from 50 Å to 150 Å, such as a pore size around 100 Å.

The term "purified" when referring to a component or fraction indicates that its relative concentration (weight of component or fraction divided by the weight of all components or fractions in the fluid mixture) is increased by at least 20%. In one series of aspects, the relative concentration is increased by at least 40%, 50%, 60%, 75%, 100%, 150%, or 200%, 300%, 400%, or 500%. A component or fraction can also be said to be purified when the relative concentration of components from which it is purified (weight of component or fraction from which it is purified divided by the weight of all components or fractions in the fluid mixture) is decreased by at least 20%, 40%, 50%, 60%, 75%, 85%, 95%, 98% or 100%. In still another series of aspects, the component or fraction is purified to a relative concentration of at least 50%, 65%, 75%, 85%, 90%, 97%, 98%, or 99%. When a component or fraction in some aspects is said to be "separated" from other components or fractions, it will be understood that the component or fraction is "purified".

The term "polypeptide of interest", as used herein, refers to any peptide, polypeptide or protein that one needs to have in purified form. The term includes synthetic, semi-recombinant or recombinant peptides, polypeptides and proteins. In some aspects, the "polypeptide of interest" is a peptide, polypeptide or protein which is suitable for treating diabetes such as e.g. an insulin peptide (e.g. human insulin, an insulin analogue or an insulin derivative), a glucagon-like peptide, a GLP-1 peptide (e.g. human GLP-1, a GLP-1 analogue or a GLP-1 derivative)) or an amylin peptide.

In one aspect of the invention the polypeptide of interest is a glucagon-like peptide such as e.g. GLP-1, a GLP-1 analogue, a GLP-1 derivative, exendin-4 or exendin-3. In one aspect of the invention the polypeptide of interest is a GLP-1 analogue or derivative. In one aspect of the invention the polypeptide of interest is a GLP-1 derivative. In one aspect of the invention the polypeptide of interest is produced by recombinant technology.

The term "impurity", as used herein refers to a component present in the fluid mixture containing the polypeptide of interest which is not the polypeptide of interest and which has to be separated from the polypeptide of interest. This "impurity" may include host cell proteins, polypeptides or peptides, other unwanted forms of the recombinant polypeptide, such as glycosylated, deamidated, or oxidized forms, and other components present in the fluid mixture.

In some aspects the impurity is a recombinant protein. In some aspects, the "impurity" is a peptide, polypeptide or a protein similar to the polypeptide of interest (also herein described as a "related impurity") which has structural resemblance to the polypeptide of interest, such as a glycosylated form, a deamidated form, a truncated form, an extended form, a deamidated form, an incorrectly folded form, or an oxidized form of said polypeptide of interest, a form with undesired glycosylation, a form resulting from racemization, a form lacking amino acids in the intra-peptide chain, a form having extra amino acids in the intra-peptide chain and a form wherein an acylation has taken place on another residue than desired. In some aspects the related impurity is a peptide, polypeptide or protein with a hydrophobicity which is similar to the polypeptide of interest. In some aspects the related impurity is a peptide, polypeptide or protein which has structural resemblance and a hydrophobicity which is similar to the polypeptide of interest.

The relation between the "polypeptide of interest" and the "unwanted component" in the fluid mixture to be purified according to the method of the invention may be e.g. at least 1:1 such as 2:1, i.e. when there is 1 equivalent of "unwanted component" in the fluid mixture there are at least 2 equivalents of the "polypeptide of interest". In one aspect of the invention the relation between the "polypeptide of interest" and the "unwanted component" in the fluid mixture is at least 4:1, in another aspect the relation is at least 6:1, in another aspect the relation is at least 8:1, in another aspect the relation is at least 9:1, in another aspect the relation is at least 14:1, in another aspect the relation is at least 19:1, in another aspect the relation is at least 20:1, in another aspect the relation is at least 50:1, and in yet another aspect the relation is at least 90:1.

The terms "about" or "approximately" as used herein means in reasonable vicinity of the stated numerical value, such as plus or minus 10%, or for pH values plus or minus 0.2.

The term "glucagon-like peptide" as used herein means the glucagon family of peptides, exendins and analogues and derivatives thereof. The glucagon family of peptides are encoded by the pre-proglucagon gene and encompasses three small peptides with a high degree of homology, i.e. glucagon (1-29), GLP-1 (1-37) and GLP-2 (1-33). Exendins are peptides expressed in lizards and like GLP-1, are insulinotropic. Examples of exendins are exendin-3 and exendin-4.

The term "analogue" as used herein refers to a modified glucagon-like peptide wherein one or more amino acid residues of the glucagon-like peptide have been substituted by other amino acid residues and/or wherein one or more amino acid residues have been deleted from the glucagon-like peptide and/or wherein one or more amino acid residues have been added to the glucagon-like peptide. Such addition or deletion of amino acid residues can e.g. take place at the N-terminal of the glucagon-like peptide and/or at the C-terminal of the peptide. A simple system is used to describe analogues: for example $Arg^{34}$-GLP-1(7-37) designates a GLP-1(7-37) analogue wherein the naturally occurring lysine at position 34 has been substituted with arginine. Whenever the term "amino acid" is used it has to be under-stood to indicate the L-isomer, if the optical isomer is not stated otherwise.

The term "amino acid" includes proteogenic amino acids (encoded by the genetic code, including natural amino acids, and standard amino acids), as well as non-proteogenic (not found in proteins, and/or not coded for in the standard genetic code), and synthetic amino acids. Thus, the amino acids may be selected from the group of proteinogenic amino acids, non-proteinogenic amino acids, and/or synthetic amino acids.

Non-limiting examples of amino acids which are not encoded by the genetic code are gamma-carboxyglutamate, ornithine, and phosphoserine. Non-limiting examples of synthetic amino acids are the D-isomers of the amino acids such as D-alanine and D-leucine, Aib (α-aminoisobutyric acid), β-alanine, and des-amino-histidine (desH, alternative name imidazopropionic acid, also abbreviated Imp).

Likewise, standard single letter abbreviation for amino acids is used according to IUPAC-IUB nomenclature.

In one aspect an analogue according to the invention comprises up to 17 modifications (substitutions, deletions, additions) relative to the glucagon-like peptide. In one aspect an analogue comprises less than 16 modifications (substitutions, deletions, additions) relative to the glucagon-like peptide. In one aspect an analogue comprises less than 15 modifications (substitutions, deletions, additions) relative to the glucagon-like peptide. In another aspect an analogue comprises less than 14 modifications (substitutions, deletions, additions) relative to the glucagon-like peptide. In another aspect an analogue comprises less than 13 modifications (substitutions, deletions, additions) relative to the glucagon-like peptide. In another aspect an analogue comprises less than 12 modifications (substitutions, deletions, additions) relative to the glucagon-like peptide. In another aspect an analogue comprises less than 11 modifications (substitutions, deletions, additions) relative to the glucagon-like peptide. In another aspect an analogue comprises less than 10 modifications (substitutions, deletions, additions) relative to the glucagon-like peptide. In another aspect an analogue comprises less than 9 modifications (substitutions, deletions, additions) relative to the glucagon-like peptide. In another aspect an analogue comprises less than 8 modifications (substitutions, deletions, additions) relative to the glucagon-like peptide. In one aspect an analogue comprises less than 7 modifications (substitutions, deletions, additions) relative to the glucagon-like peptide. In one aspect an analogue comprises less than 6 modifications (substitutions, deletions, additions) relative to the glucagon-like peptide. In another aspect an analogue comprises less than 5 modifications (substitutions, deletions, additions) relative to the glucagon-like peptide. In another aspect an analogue comprises less than 4 modifications (substitutions, deletions, additions) relative to the glucagon-like peptide. In another aspect an analogue comprises less than 3 modifications (substitutions, deletions, additions) relative to the glucagon-like peptide. In another aspect an analogue comprises less than 2 modifications (substitutions, deletions, additions) relative to the glucagon-like peptide.

The term "lipophilically modified peptide" as used herein is a peptide comprising one or more lipophilic groups, such as lipophilic sidechains, covalently attached to one or more amino acids of the peptide. In one aspect according to the invention a lipophilic group is a lipophilic sidechain. The peptide that is lipophilically modified may be prepared by any suit-able methodology, for example by attaching the lipophilic group(s) by conjugation chemistry such as by alkylation, acylation, ester formation, amide formation or maleimide coupling. In one aspect according to the present invention, the lipophilically modified peptides according to the invention have substantially the same activity relative to the same peptide, which is not lipophilically modified.

In one aspect, the lipophilically modified glucagon-like peptide to be included in the pharmaceutical composition of the present invention, is a GLP-1 agonist composed of at least five constituent amino acids connected by peptide bonds and an acyl group attached thereof.

The term "GLP-1 agonist" as used herein refers to any lipophilically modified glucagon-like peptide which fully or partially activates the human GLP-1 receptor. In a preferred aspect, the "GLP-1 agonist" is any lipophilically modified glucagon-like peptide that binds to a GLP-1 receptor, preferably with an affinity constant (KD) or a potency ($EC_{50}$) of below 1 µM, e.g., below 100 nM as measured by methods known in the art (see e.g., WO 98/08871) and exhibits insulinotropic activity, where insulinotropic activity may be measured in vivo or in vitro assays known to those of ordinary skill in the art. For example, the GLP-1 agonist may be administered to an animal and the insulin concentration measured over time.

In one aspect, the lipophilically modified glucagon-like peptide of the present invention is acylated, i.e., it has an acyl group attached, as the lipophilical modification.

An acyl group (IUPAC name: alkanoyl) is a functional group derived by the removal of one or more hydroxyl groups from an oxoacid. In organic chemistry, the acyl group is derived from a carboxylic acid of the form RCOOH. It therefore has the formula RC(=O)—, with a double bond between the carbon and oxygen atoms (i.e., a carbonyl group), and a single bond between R and the carbon. Acyl groups can also be derived from other types of acids such as sulfonic acids, phosphonic acids, and others.

In the acylated modified glucagon-like peptide compounds of the invention, the acyl group contains a functional group which can be attached to one of the following functional groups of an amino acid of the parent glucagon-like peptide:

(a) the amino group attached to the alpha-carbon of the N-terminal amino acid, (b) the carboxy group attached to the alpha-carbon of the C-terminal amino acid, (c) the epsilon-amino group of any Lys residue, (d) the carboxy group of the R group of any Asp and Glu residue, (e) the hydroxy group of the R group of any Tyr, Ser and Thr residue, (f) the amino group of the R group of any Trp, Asn, Gln, Arg, and H is residue, or (g) the thiol group of the R group of any Cys residue.

In one aspect, the acyl group is attached to the carboxy group of the R group, i.e., the side chain of any Asp and Glu residue. In another aspect, the acyl group is attached to the carboxy group attached to the alpha-carbon of the C-terminal amino acid. In yet another aspect, the acyl group is attached to the epsilon-amino group of any Lys residue.

In one aspect of the invention, the acyl group is attached to the parent glucagon-like peptide by means of a spacer. A spacer must contain at least two functional groups, one to attach to a functional group of the acyl group and the other to a functional group of the parent glucagon-like peptide.

In one aspect, the acyl group is a straight-chain or branched fatty acid. In one aspect, the acyl group has the formula $CH_3(CH_2)_nCO$—, wherein n is an integer from 4 to 38, such as an integer from 12 to 38. In one aspect the acyl group is selected from the group consisting of: $CH_3(CH_2)_{12}CO$—, $CH_3(CH_2)_{14}CO$—, $CH_3(CH_2)_{16}CO$—, $CH_3(CH_2)_{18}CO$—, $CH_3(CH_2)_{20}CO$— and $CH_3(CH_2)_{22}CO$—. In another aspect, the acyl group is tetradecanoyl. In yet another aspect, the acyl group is hexadecanoyl.

In a further aspect of the present invention, the acyl group has a group which is negatively charged such as a carboxylic acid group. For example, the acyl group may be a straight-chain or branched alkane α,ω-dicarboxylic acid of the formula $HOOC(CH_2)_mCO$—, wherein m is an integer from 4 to 38, such as an integer from 12 to 38. In one aspect the acyl group is selected from the group consisting of: $HOOC(CH_2)_{14}CO$—, $HOOC(CH_2)_{16}CO$—, $HOOC(CH_2)_{18}CO$—, $HOOC(CH_2)_{20}CO$— or $HOOC(CH_2)_{22}CO$—.

In one aspect, the spacer is a dipeptide such as Gly-Lys or an amino acid residue except Cys or Met. For purposes of the present invention, the phrase "a dipeptide such as Gly-Lys" means any combination of two amino acids except Cys or Met, in one aspect a dipeptide wherein the C-terminal amino acid residue is Lys, H is or Trp, such as Lys, and the N-terminal amino acid residue is Ala, Arg, Asp, Asn, Gly, Glu, Gln, Ile, Leu, Val, Phe, Pro, Ser, Tyr, Thr, Lys, His and Trp. In one aspect, an amino group of the parent peptide forms an amide bond with a carboxylic group of the amino acid residue or dipeptide spacer, and an amino group of the amino acid residue or dipeptide spacer forms an amide bond with a carboxyl group of the acyl group.

Examples of spacers according to the invention include lysyl, glutamyl, asparagyl, glycyl, beta-alanyl and gamma-aminobutanoyl, each of which constitutes an individual aspect. In one aspect spacers are glutamyl and beta-alanyl. When the spacer is Lys, Glu or Asp, the carboxyl group thereof may form an amide bond with an amino group of the amino acid residue, and the amino group thereof may form an amide bond with a carboxyl group of the acyl group. When Lys is used as the spacer, a further spacer may in some instances be inserted between the ε-amino group of Lys and the acyl group. In one aspect, such a further spacer is succinic acid which forms an amide bond with the ε-amino group of Lys and with an amino group present in the acyl group. In another aspect such a further spacer is Glu or Asp which forms an amide bond with the ε-amino group of Lys and another amide bond with a carboxyl group present in the acyl group, that is, the acyl group is a $N^\epsilon$-acylated lysine residue.

In another aspect, the spacer is an unbranched alkane α,ω-dicarboxylic acid group having from 1 to 7 methylene groups, which spacer forms a bridge between an amino group of the parent peptide and an amino group of the substituent. In one aspect the spacer is succinic acid.

In a further aspect, the acyl group with the attached spacer is a group of the formula $CH_3(CH_2)_pNH$—$CO(CH_2)_qCO$—, wherein p is an integer from 8 to 33, alternatively from 12 to 28 and q is an integer from 1 to 6, alternatively 2.

In a further aspect, the acyl group with the attached spacer is a group of the formula $CH_3(CH_2)_nCO$—$NHCH(COOH)(CH_2)_2CO$—, wherein r is an integer from 4 to 24, such as from 10 to 24.

In a further aspect, the acyl group with the attached spacer is a group of the formula $CH_3(CH_2)_sCO$—$NHCH((CH_2)_2COOH)CO$—, wherein s is an integer from 4 to 24, such as from 10 to 24.

In a further aspect, the acyl group is a group of the formula $COOH(CH_2)_tCO$— wherein t is an integer from 6 to 24.

In a further aspect, the acyl group with the attached spacer is a group of the formula —$NHCH(COOH)(CH_2)_4NH$—$CO(CH_2)_uCH_3$, wherein u is an integer from 8 to 18.

In a further aspect, the acyl group with the attached spacer is a group of the formula $CH_3(CH_2)_nCO$—$NH$—$(CH_2)_z$—$CO$, wherein v is an integer from 4 to 24 and z is an integer from 1 to 6.

In a further aspect, the acyl group with the attached spacer is a group of the formula —$NHCH(COOH)(CH_2)_4NH$—$COCH((CH_2)_2COOH)NH$—$CO(CH_2)_wCH_3$, wherein w is an integer from 10 to 16.

In a further aspect, the acyl group with the attached spacer is a group of the formula —$NHCH(COOH)(CH_2)_4NH$—$CO(CH_2)_2CH(COOH)NHCO(CH_2)_xCH_3$, wherein x is zero or an integer from 1 to 22, such as 10 to 16.

The invention also provides, an lipophilically modified glucagon-like peptide, wherein the glucagon-like peptide is a GLP-1(7-37) analogue which is selected from the group consisting of $Arg^{34}$GLP-1(7-37), $Aib^{8,22,35}$GLP-1(7-37), $Aib^{8,35}$GLP-1(7-37), $Aib^{8,22}$GLP-1(7-37), $Aib^{8,22,35}$ $Lys^{37}$GLP-1(7-37), $Aib^{8,35}Lys^{37}$GLP-1(7-37), $Aib^{8,34}$GLP-1(7-37) and $Aib^{8,22}Lys^{37}$GLP-1(7-38), [desaminoHis$^7$, Glu$^{22}$,Arg$^{26}$,Arg$^{34}$,Lys$^{37}$]GLP-1(7-37)amide, [desamino-His$^7$,Arg$^{34}$]GLP-1-(7-37), [Aib$^8$,Glu$^{22}$,Arg$^{26}$,Arg$^{34}$,Lys$^{37}$] GLP-1-(7-37)amide, [DesaminoHis$^7$, Glu$^{22}$ Arg$^{26}$, Arg$^{34}$, Phe(m-CF$_3$)$^{28}$]GLP-1-(7-37)amide, [DesaminoHis$^7$,Glu$^{22}$, Arg$^{26}$,Arg$^{34}$]GLP-1-(7-37)-Lys, [DesaminoHis$^7$,Glu$^{22}$, Arg$^{26}$,Arg$^{34}$]GLP-1-(7-37)-Lys, [desaminoHis$^7$,Arg$^{26}$, Arg$^{34}$,]GLP-1-(7-37)-Lys, [DesaminoHis$^7$,Glu$^{22}$,Arg$^{26}$, Arg$^{34}$,Lys$^{37}$]GLP-1-(7-37)amide, [DesaminoHis$^7$,Arg$^{26}$, Arg$^{34}$,Lys$^{37}$]GLP-1-(7-37)amide, [DesaminoHis$^7$,Glu$^{22}$, Arg$^{26}$,Arg$^{34}$,Lys$^{37}$]GLP-1-(7-37), [DesaminoHis$^7$,Arg$^{26}$, Arg$^{34}$,Lys$^{37}$]GLP-1-(7-37), [DesaminoHis$^7$,Glu$^{22}$,Arg$^{26}$, Glu$^{30}$,Arg$^{34}$,Lys$^{37}$]GLP-1-(7-37), [Aib$^8$, Glu$^{22}$, Arg$^{26}$, Arg$^{34}$,]GLP-1-7-37)-Lys, and Gly$^8$-GLP-1(7-36), wherein said GLP-1 analogue is acylated.

In yet another aspect the lipophilically modified glucagon-like peptide as used herein means acylated GLP-1(7-37) and insulinotropic analogues thereof. Non-limiting examples of GLP-1 analogues and acylated GLP-1 analogues are GLP-1(7-36) amide, Arg$^{34}$-GLP-1(7-37), Gly$^8$-GLP-1(7-37), Val$^8$-GLP-1(7-36)-amide, Val$^8$Asp$^{22}$-GLP-1 (7-37), desamino-His$^7$, Arg$^{26}$, Lys$^{34}$(N$^\epsilon$-(γ-Glu(N$^\alpha$-hexadecanoyl)))-GLP-1(7-37), desamino-His$^7$, Arg$^{26}$, Lys$^{34}$ (N$^\epsilon$-octanoyl)-GLP-1(7-37), Arg$^{26,34}$, Lys$^{38}$(N$^\epsilon$-(ω-carboxypentadecanoyl))-GLP-1(7-38), Arg$^{26,34}$, Lys$^{36}$(N$^\epsilon$ (γ-Glu(N$^\alpha$-hexadecanoyl)))-GLP-1(7-36) and Arg$^{34}$, Lys$^{26}$ (N$^\epsilon$-(γ-Glu(N$^\alpha$-hexadecanoyl)))-GLP-1(7-37).

In one aspect the lipophilically modified glucagon-like peptide of the present invention is dipeptidyl aminopeptidase IV protected. The term "dipeptidyl aminopeptidase IV protected" as used herein means a compound, e.g. an acylated GLP-1 analogue, which is more resistant to dipeptidyl aminopeptidase IV (DPP-IV) than the native compound, e.g. GLP-1(7-37). Resistance of a lipophilically modified glucagon-like peptide towards degradation by dipeptidyl aminopeptidase IV is determined by the degradation assay described below.

Aliquots of the lipophilically modified glucagon-like peptide (5 nmol) are incubated at 37° C. with 1 μl of purified dipeptidyl aminopeptidase IV corresponding to an enzymatic activity of 5mU for 10-180 minutes in 100 μl of 0.1M triethylamine-HCl buffer, pH 7.4. Enzymatic reactions are terminated by the addition of 5 μl of 10% trifluoroacetic acid, and the peptide degradation products are separated and quantified using HPLC analysis. In one method for performing this analysis the mixtures are applied onto a Vydac C18 widepore (30 nm pores, 5 μm particles) 250×4.6 mm column ($C_{18}$-substituted (octadecyl-dimethylsilyl) silica resin) and eluted at a flow rate of 1 ml/min with linear stepwise gradients of acetonitrile in 0.1% trifluoroacetic acid (0% acetonitrile for 3 min., 0-24% acetonitrile for 17 min., 24-48% acetonitrile for 1 min.) according to Siegel et al. [Regul. Pept. (1999) 79:93-102] and Mentlein et al. [Eur. J. Biochem. (1993) 214:829-35]. Peptides and their degradation products may be monitored by their absorbance at 220 nm (peptide bonds) or 280 nm (aromatic amino acids), and are quantified by integration of their peak areas related to those of standards. The rate of hydrolysis of a lipophilically modified glucagon-like peptide by dipeptidyl aminopeptidase IV is estimated at incubation times which result in less than 10% of the lipophilically modified glucagon-like peptide being hydrolysed.

In yet another aspect, the lipophilically modified glucagon-like peptide to be included in the pharmaceutical compositions of the present invention is lipophilically modified GLP-2 or an analogue thereof. Where the lipophilically modified glucagon-like peptide to be included in the pharmaceutical compositions of the present invention is lipophilically modified GLP-2 or an analogue thereof, the lipophilically modified GLP-2 or an analogue thereof is present in a concentration from about 1 mg/ml to about 100 mg/ml, more preferably in a concentration from about 1 mg/ml to about 10 mg/ml.

In yet another aspect the lipophilically modified glucagon-like peptide is lipophilically modified exendin-4 or lipophilically modified exendin-3 or analogues thereof. Examples of exendins as well as analogues thereof to be included within the present invention are those disclosed in WO 97/46584, U.S. Pat. No. 5,424,286 and WO 01/04156. U.S. Pat. No. 5,424,286 describe a method for stimulating insulin release with an exendin peptide. WO 97/46584 describes truncated versions of exendin peptide(s). The disclosed peptides increase secretion and biosynthesis of insulin, but reduce those of glucagon. WO 01/04156 describes exendin-4 analogues and derivatives as well as the preparation of these molecules.

The term "exendin-4 peptide" as used herein means exendin-4(1-39), an exendin-4(1-39) analogue, an exendin-4(1-39) derivative or a derivative of an exendin-4(1-39) analogue, insulinotropic fragments thereof, insulinotropic analogues thereof and insulinotropic derivatives thereof. Insulinotropic fragments of exendin-4 are insulinotropic peptides for which the entire sequence can be found in the sequence of exendin-4 and where at least one terminal amino acid has been deleted. Examples of insulinotropic fragments of exendin-4(1-39) are exendin-4(1-38) and exendin-4(1-31).

The insulinotropic property of a compound may be determined by in vivo or in vitro assays well known in the art. For instance, the compound may be administered to an animal and monitoring the insulin concentration over time. Insulinotropic analogues of exendin-4(1-39) refer to the respective molecules wherein one or more of the amino acids residues have been exchanged with other amino acid residues and/or from which one or more amino acid residues have been deleted and/or from which one or more amino acid residues have been added with the proviso that said analogue either is insulinotropic or is a prodrug of an insulinotropic compound. An example of an insulinotropic analogue of exendin-4(1-39) is $Ser^2Asp^3$-exendin-4(1-39) wherein the amino acid residues in position 2 and 3 have been replaced with serine and aspartic acid, respectively (this particular analogue also being known in the art as exendin-3). Insulinotropic derivatives of exendin-4(1-39) and analogues thereof are what the person skilled in the art considers to be derivatives of these peptides, i.e., having at least one substituent which is not present in the parent peptide molecule with the proviso that said derivative either is insulinotropic or is a prodrug of an insulinotropic compound. Examples of substituents are amides, carbohydrates, alkyl groups, esters and lipophilic substituents. An example of an insulinotropic derivative of exendin-4(1-39) and analogues thereof is $Tyr^{31}$-exendin-4(1-31)-amide.

The term "stable exendin-4 compound" as used herein means a chemically modified exendin-4(1-39), i.e., an acylated exendin-3 or acylated exendin-4 analogue which exhibits an in vivo plasma elimination half-life of at least 10 hours in man, as determined by conventional methods.

In one aspect the lipophilically modified glucagon-like peptide of the present invention is insulinotropic. The term "insulinotropic" as used herein referring to a lipophilically modified glucagon-like peptide means the ability to stimulate secretion of insulin in response to an increased plasma glucose level. Insulinotropic peptides and compounds are agonists of the GLP-1 receptor. The insulinotropic property of a compound may be determined by in vitro or in vivo assays known in the art. The following in vitro assay may be used to determine the insulinotropic nature of a compound such as a peptide. Preferably insulinotropic compounds exhibit an $EC_{50}$ value in below assay of less than 5 nM, even more preferably $EC_{50}$ values less than 500 pM.

Baby hamster kidney (BHK) cells expressing the cloned human GLP-1 receptor (BHK 467-12A) are grown in DMEM media with the addition of 100 IU/ml penicillin, 100 μl/ml streptomycin, 10% fetal calf serum and 1 mg/ml Geneticin G-418 (Life Technologies, Grand Island, N.Y.). Plasma membranes are prepared by homogenization in buffer (10 mM Tris-HCl, 30 mM NaCl and 1 mM dithiothreitol, pH 7.4, containing, in addition, 5 mg/ml leupeptin (Sigma, St. Louis, Mo.), 5 mg/l pepstatin (Sigma, St. Louis, Mo.), 100 mg/l bacitracin (Sigma, St. Louis, Mo.), and 16 mg/l aprotinin (Calbiochem-Novabiochem, La Jolla, Calif.)). The homogenate is centrifuged on top of a layer of 41% w/w sucrose. The white band between the two layers is diluted in buffer and centrifuged. Plasma membranes are stored at −80° C. until further use.

The functional receptor assay is carried out by measuring cAMP as a response to stimulation by the insulinotropic peptide or insulinotropic compound. Incubations are carried out in 96-well microtiter plates in a total volume of 140 ml and with the following final concentrations: 50 mM Tris-HCl, 1 mM EGTA, 1.5 mM $MgSO_4$, 1.7 mM ATP, 20 mM GTP, 2 mM 3-isobutyl-1-methylxanthine (IBMX), 0.01% w/v Tween-20, pH 7.4. Compounds are dissolved and diluted in buffer. GTP is freshly prepared for each experiment: 2.5 μg of membrane is added to each well and the mixture is incubated for 90 min. at room temperature in the dark with shaking. The reaction is stopped by the addition of 25 ml, 0.5M HCl. Formed cAMP is measured by a scintillation proximity assay (RPA 542, Amersham, UK). A dose-response curve is plotted for the compound and the $EC_{50}$ value may be calculated using GraphPad Prism software.

The production of polypeptides and peptides, such as glucagon-like peptides to be lipophilically modified, is well known in the art. Polypeptides or peptides may for instance be produced by classical peptide synthesis, e.g. solid phase peptide synthesis using t-Boc or Fmoc chemistry or other well established techniques, see e.g. Greene and Wuts [Protective Groups in Organic Synthesis, John Wiley & Sons (1999)]. The polypeptides or peptides may also be produced by a method which comprises culturing a host cell containing a DNA sequence encoding the (poly)peptide and capable of expressing the (poly)peptide in a suitable nutrient medium under conditions permitting the expression of the peptide. For (poly)peptides comprising non-natural amino acid residues, the recombinant cell should be modified such that the non-natural amino acids are incorporated into the (poly)peptide, for instance by use of tRNA mutants.

The term "liraglutide" as used herein is used for the glucagon-like peptide (GLP-1) derivative, $Arg^{34},Lys^{26}(N^{\epsilon}$-(γ-Glu($N^{\alpha}$-hexadecanoyl)))-GLP-1(7-37).

The invention is further summarized in the following paragraphs:
1. A method for separating on a RP-HPLC system a polypeptide of interest from at least one unwanted component in a fluid mixture, the method comprising:
   a. Introducing to the RP-HPLC system a mixture comprising the polypeptide of interest, the mixture being dissolved in a mobile phase, wherein the mobile phase has a pH value which is at least 1 unit from the pI value of the polypeptide of interest
   b. adjusting the pH of the mobile phase to a pH value which is less than 1 unit from the pI value of the polypeptide of interest, wherein the adjustment in pH is done in a step-wise procedure or with a pH gradient
   c. eluting the polypeptide of interest to provide a purified composition thereof.
2. The method according to aspect 1, wherein a step is added between step b and step c, wherein pH is again adjusted to a pH value which is at least 1 unit from the pI value of the peptide or protein to be purified, and wherein said adjustment is done in a step-wise procedure or with a pH gradient
3. The method according to aspect 1 or 2, wherein the pH value in step a. is at least 1.5 units from the pI value of the peptide or protein to be purified
4. The method according to any one of the preceding aspects, wherein the pH value in step a. is at least 2 units from the pI value of the peptide or protein to be purified
5. The method according to any one of the preceding aspects, wherein the pH value in step a. is at least 2.5 units from the pI value of the peptide or protein to be purified
6. The method according to any one of the preceding aspects, wherein the pH value in step a. is higher than the pI value of the peptide or protein to be purified
7. The method according to any one of the preceding aspects, wherein the pH value in step a. is between 5.5 and 9.0
8. The method according to any one of the preceding aspects, wherein the pH value in step a. is between 6.0 and 8.5
9. The method according to any one of the preceding aspects, wherein the pH value in step a. is between 7.0 and 8.0
10. The method according to any one of the preceding aspects, wherein the pH value in step a. is between 7.0 and 9.0
11. The method according to any one of the preceding aspects 3, wherein the pH value in step a. is approximately 8.0
12. The method according to any one of the preceding aspects, wherein the pH value in step a. is between 2.5 and 5.0
13. The method according to any one of the preceding aspects, wherein the pH value in step a. is between 2.5 and 4.0
14. The method according to any one of the preceding aspects, wherein the pH value in step a. is between 2.5 and 3.5
15. The method according to any one of the preceding aspects, wherein the pH value in step b is less than 0.8 units from the pI value of the peptide or protein to be purified
16. The method according to any one of the preceding aspects, wherein the pH value in step b is less than 0.6 units from the pI value of the peptide or protein to be purified
17. The method according to any one of the preceding aspects, wherein the pH value in step b is less than 0.5 units from the pI value of the peptide or protein to be purified
18. The method according to any one of the preceding aspects, wherein the pH value in step b is higher than the pI value of the peptide or protein to be purified
19. The method according to any one of the preceding aspects, wherein the pH value in step b is between 3.5 and 5.5
20. The method according to any one of the preceding aspects, wherein the pH value in step b is between 4.0 and 5.5
21. The method according to any one of the preceding aspects, wherein the pH value in step b is between 4.5 and 5.2
22. The method according to any one of the preceding aspects, wherein the pH value in step b is between 4.5 and 7.0
23. The method according to any one of the preceding aspects, wherein the pH value in step b is between 4.8 and 6.5
24. The method according to any one of the preceding aspects, wherein the pH value in step b is between 5.0 and 6.0
25. The method according to any one of the preceding aspects, wherein adjusting the pH of the mobile phase in step b is with a pH gradient
26. The method according to any one of the preceding aspects wherein the method comprises applying a gradient of an organic modifier simultaneously with step b to remove the unwanted impurities while retaining the target peptide on the RP-HPLC system
27. The method according to aspect 26, wherein the gradient of the organic modifier in step b is from about 25% to about 48% and the pH gradient is from pH 7.4 to 4.5
28. The method according to any one of the preceding aspects, wherein the pH gradient in step b) is from about 7.4 to about 4.5
29. The method according to any one of the preceding aspects, wherein the temperature on the RP gel is elevated
30. The method according to any one of aspects 1-28, wherein the temperature on the RP gel is between 20 and 70 degrees Celcius.
31. The method according to any one of the preceding aspects, wherein the temperature on the RP gel is elevated between 40 and 60 degrees Celcius
32. The method according to any one of the preceding aspects, wherein the temperature on the RP gel is elevated about 50 degrees Celcius
33. The method according to any one of aspects 1-28, wherein the temperature on the RP gel is about room temperature
34. The method according to any one of the preceding aspects, wherein the adsorbent used in the RP HPLC system is selected from the group consisting of: Substituted silica, such as C-4 silica, C-6 silica, C-12 silica, C-18 silica and phenyl-based silica, polymeric materials such as polystyrene, membranes, monolithic materials and filters
35. The method according to any one of the preceding aspects, wherein the adsorbent used in RP HPLC system is a gel which is substituted with a C18 (Octadecyl-dimethylsilyl) ligand and has particles which are about 15 μm and a pore size about 100 Å
36. The method according to any one of the preceding aspects, wherein the peptide or protein is selected from the group consisting of a GLP-1 peptide, an exendin peptide or a GLP-1 derivative.
37. The method according to aspect 26 or 27, wherein the organic modifier is selected from the group consisting of ethanol, methanol, propanol, and acetonitrile.

38. The method according to any one of the preceding aspects wherein the polypeptide of interest is a polypeptide suitable for treating diabetes
39. The method according to any one of any of the preceding aspects, wherein the polypeptide of interest is glucagon-like peptide or a GLP-1 agonist.
40. The method according to any one of the preceding aspects, wherein the polypeptide of interest is GLP-1 (1-37) or an analogue or derivative thereof.
41. The method according to any one of the preceding aspects, wherein the GLP-1 (1-37) or an analogue or derivative thereof is recombinantly derived.
42. The method according to any one of the preceding aspects, wherein said at least one unwanted component is another form of the said polypeptide, such as glycosylated, deamidated, or oxidized form of said polypeptide.
43. The method according to any of the preceding aspects, wherein the relation between the polypeptide of interest and the said at least one unwanted component is at least 4:1.
44. The method according to any of the preceding aspects, wherein the relation between the polypeptide of interest and the said at least one unwanted component is at least 10:1.
45. The method according to any of the preceding aspects, wherein the relation between the polypeptide of interest and the said at least one unwanted component is at least 20:1.
46. The method according to any of the preceding aspects, wherein the relation between the polypeptide of interest and the said at least one unwanted component is at least 50:1.
47. The method according to any of the preceding aspects, wherein the relation between the polypeptide of interest and the said at least one unwanted component is at least 80:1.

EXAMPLES

Example 1

RP HPLC Purification of N-Epsilon$^{26}$-[2-(-2-[2-(2-[2-(2-[4-(17-Carboxyheptadecanoylamino)-4(S)-Carboxybutyrylamino]Ethoxy)Ethoxy]Acetylamino)Ethoxy]Ethoxy)Acetyl][Aib$^8$,Arg$^{34}$]GLP-1(7-37) Petide N-$\epsilon^{26}$-[2-(-2-[2-(2-[2-(2-[4-(17-Carboxyheptadecanoylamino)-4(s)-carboxybutyrylamino]ethoxy)ethoxy]acetylamino)ethoxy]ethoxy)acetyl][Aib$^8$,Arg$^{34}$]GLP-1(7-37)petide was produced synthetically. The acylated mixture was first purified by conventional anion exchange, the obtained pool containing N-$\epsilon^{26}$-[2-(-2-[2-(2-[2-(2-[4-(17-Carboxyheptadecanoylamino)-4(s)-carboxybutyrylamino]ethoxy)ethoxy]acetylamino)ethoxy]ethoxy)acetyl][Aib$^8$,Arg$^{34}$] GLP-1(7-37)petide and related impurities was then diluted by water. 10 ml of fluid mixture (4.5 mg/ml) was loaded onto a 20 ml C$_{18}$-substituted (octadecyl-dimethylsilyl) silica resin (particle size: 15 µm) equilibrated with about 120 ml of 10 mmol/kg citrate buffer, 50 mmol/kg NaCl, 25% (w/w) ethanol, pH 4.5. The column was washed with 60 ml equilibration solution and elution was performed with a linear gradient of 41-46% (w/w) ethanol (10 mmol/kg citrate buffer, 50 mmol/kg NaCl) during 400 ml. The chromatographic temperature was kept at 50° C.

A chromatogram of the preparative purification is shown in FIG. 1. From the chromatographic profile it can be observed that the impurity 2 is separated from the peptide of interest peak. The relative retention volume of impurity 2 to peptide of interest is about 0.93, a good separation between impurity 2 and peptide of interest was observed at pI value.

Example 2

RP HPLC Purification of N-Epsilon$^{26}$-[2-(-2-[2-(2-[2-(2-[4-(17-Carboxyheptadecanoylamino)-4(S)-Carboxybutyrylamino]Ethoxy)Ethoxy]Acetylamino)Ethoxy]Ethoxy)Acetyl][Aib$^8$,Arg$^{34}$]GLP-1(7-37) Petide N-$\epsilon^{26}$-[2-(-2-[2-(2-[2-(2-[4-(17-Carboxyheptadecanoylamino)-4(s)-carboxybutyrylamino]ethoxy)ethoxy]acetylamino)ethoxy]ethoxy)acetyl][Aib$^8$,Arg$^{34}$]GLP-1(7-37)petide was produced synthetically. The acylated mixture was first purified by conventional anion exchange, the obtained pool containing N-$\epsilon^{26}$-[2-(-2-[2-(2-[2-(2-[4-(17-Carboxyheptadecanoylamino)-4(s)-carboxybutyrylamino]ethoxy)ethoxy]acetylamino)ethoxy]ethoxy)acetyl][Aib$^8$,Arg$^{34}$] GLP-1(7-37)petide and related impurities was then diluted by water. 10 ml of fluid mixture (4.5 mg/ml) was loaded onto a 20 ml C$_{18}$-substituted (octadecyl-dimethylsilyl) silica resin (particle size: 15 µm) equilibrated with about 120 ml of 10 mmol/kg citrate buffer, 50 mmol/kg NaCl, 25% (w/w) ethanol, pH 5.2. The column was washed with 60 ml equilibration solution and elution was performed with a linear gradient of 39-44% (w/w) ethanol (10 mmol/kg citrate buffer, 50 mmol/kg NaCl) during 400 ml. The chromatographic temperature was kept at 50° C.

Figure 2:
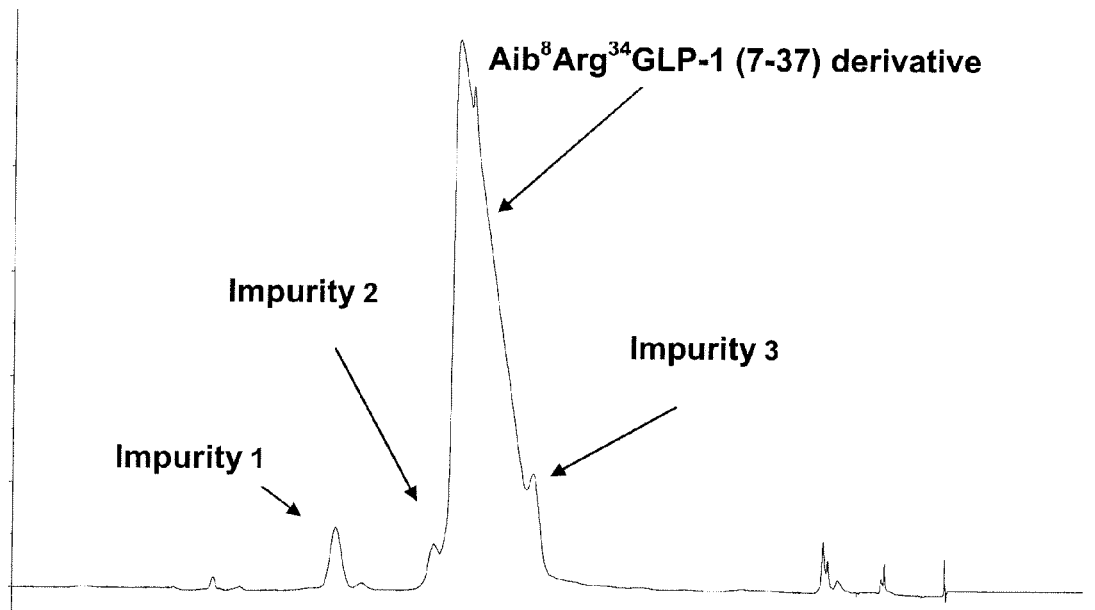
FIG. 2. Chromatogram of $AU_{280}$ versus time for the separation, elution was performed at pH 5.2

A chromatogram of the preparative purification is shown in FIG. 2. From the chromatographic profile it can be observed that the impurity 2 is separated from the peptide of interest peak. The relative retention volume of impurity 2 to peptide of interest is about 0.94, a good separation between impurity 2 and peptide of interest was obtained at a pH close to pI value.

Example 3

RP HPLC Purification of N-Epsilon$^{26}$-[2-(-2-[2-(2-[2-(2-[4-(17-Carboxyheptadecanoylamino)-4(S)-Carboxybutyrylamino]Ethoxy)Ethoxy]Acetylamino)Ethoxy]Ethoxy)Acetyl][Aib$^8$,Arg$^{34}$]GLP-1(7-37) Petide N-$\epsilon^{26}$-[2-(-2-[2-(2-[2-(2-[4-(17-Carboxyheptadecanoylamino)-4(s)-carboxybutyrylamino]ethoxy)ethoxy]acetylamino)ethoxy]ethoxy)acetyl][Aib$^8$,Arg$^{34}$]GLP-1(7-37)petide was produced synthetically. The acylated mixture was first purified by conventional anion exchange, the obtained pool containing N-$\epsilon^{26}$-[2-(-2-[2-(2-[2-(2-[4-(17-Carboxyheptadecanoylamino)-4(s)-carboxybutyrylamino]ethoxy)ethoxy]acetylamino)ethoxy]ethoxy)acetyl][Aib$^8$,Arg$^{34}$] GLP-1(7-37)petide and related impurities was then diluted by water. 10 ml of fluid mixture (4.5 mg/ml) was loaded onto a 20 ml C$_{18}$-substituted (octadecyl-dimethylsilyl) silica resin (particle size: 15 µm) equilibrated with about 120 ml of 10 mmol/kg citrate buffer, 50 mmol/kg NaCl, 25% (w/w) ethanol, pH 5.5. The column was washed with 60 ml equilibration solution and elution was performed with a linear gradient of 38-43% (w/w) ethanol (10 mmol/kg citrate buffer, 50 mmol/kg NaCl) during 400 ml. The chromatographic temperature was kept at 50° C.

Figure 3:
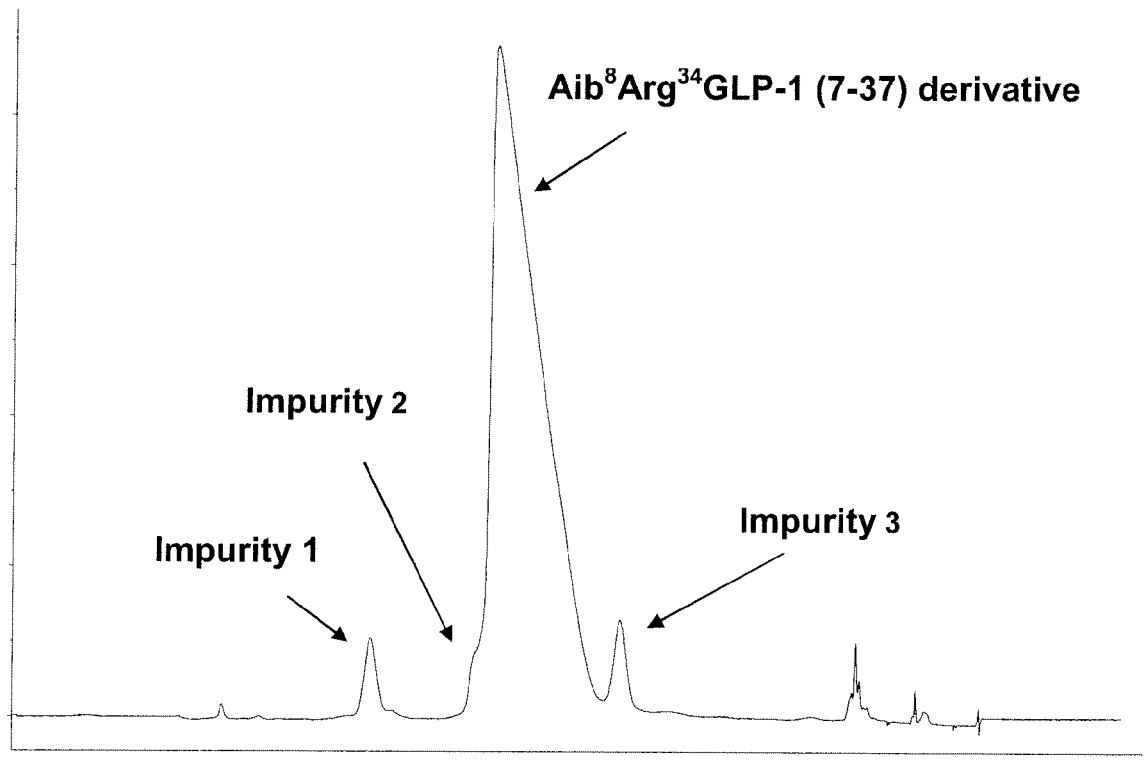
FIG. 3. Chromatogram of $AU_{280}$ versus time for the separation, elution was performed at pH 5.5
Figure 4:
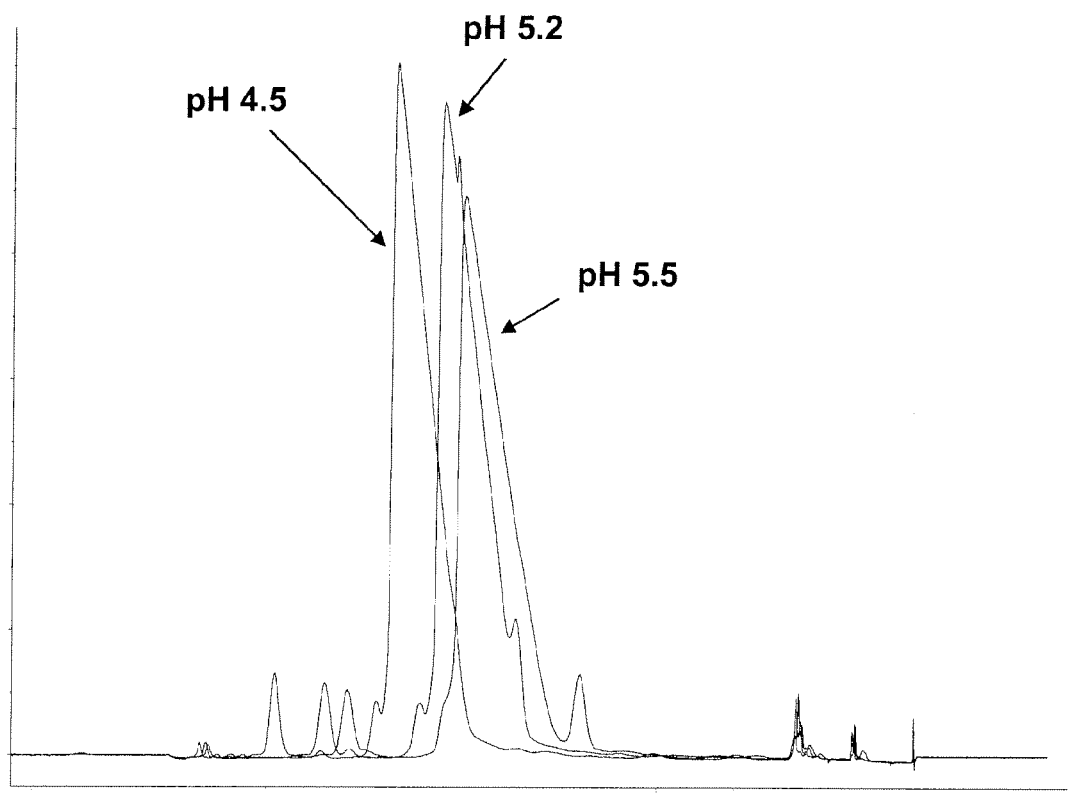
FIG. 4. Overlapped chromatograms from experiments performed at different pH of 4.5, 5.2 and 5.5

A chromatogram of the preparative purification is shown in FIG. 3. From the chromatographic profile it can be observed that the impurity 2 is separated from the peptide of interest peak. The relative retention volume of impurity 2 to peptide of interest is about 0.96. The results indicated that the best separation of impurity 2 is obtained at a pH at pI or close to pI. No separation of impurity 2 and peptide of interest was observed at pH higher than 5.5 (figure is not shown).

Example 4

RP HPLC Purification of N-Epsilon$^{26}$-[2-(-2-[2-(2-[2-(2-[4-(17-Carboxyheptadecanoylamino)-4(S)-Carboxybutyrylamino]Ethoxy)Ethoxy]Acetylamino)Ethoxy]Ethoxy)Acetyl][Aib$^8$,Arg$^{34}$]GLP-1(7-37) Petide N-ε$^{26}$-[2-(–2-[2-(2-[2-(2-[4-(17-Carboxyheptadecanoylamino)-4(s)-carboxybutyrylamino]ethoxy)ethoxy]acetylamino)ethoxy]ethoxy)acetyl][Aib$^8$,Arg$^{34}$]GLP-1(7-37)petide produced synthetically. The acylated mixture was first purified by conventional anion exchange, the obtained pool containing N-ε$^{26}$-[2-(–2-[2-(2-[2-(2-[4-(17-Carboxyheptadecanoylamino)-4(s)-carboxybutyrylamino]ethoxy)ethoxy]acetylamino)ethoxy]ethoxy)acetyl][Aib$^8$,Arg$^{34}$]GLP-1(7-37)petide) and related impurities were then diluted by water. 10 ml of fluid mixture (4.5 mg/ml) was loaded onto a 20 ml $C_{18}$-substituted (dimethylsilyl) silica resin (particle size: 15 μm) equilibrated with about 40 ml of 10 mmol/kg citrate buffer, 125 mmol/kg NaCl, 25% (w/w) ethanol, pH 7.4. The column was washed by a linear gradient of 25-48% (w/w) ethanol (10 mmol/kg citrate buffer, 125 mmol/kg NaCl, pH 4.5) for 60 ml, then isocratic wash at EtOH 48% (w/w) and pH 4.5 for 40 ml (10 mmol/kg citrate buffer, 50 mmol/kg $NaCl_3$). The target polypeptide was then eluted by a linear pH gradient elution from pH 4.5 to 7.4 (10 mmol/kg citrate buffer, 125 mmol/kg NaCl, EtOH 48% w/w) during 300 ml. The chromatographic temperature was kept at 50° C.

Figure 5:
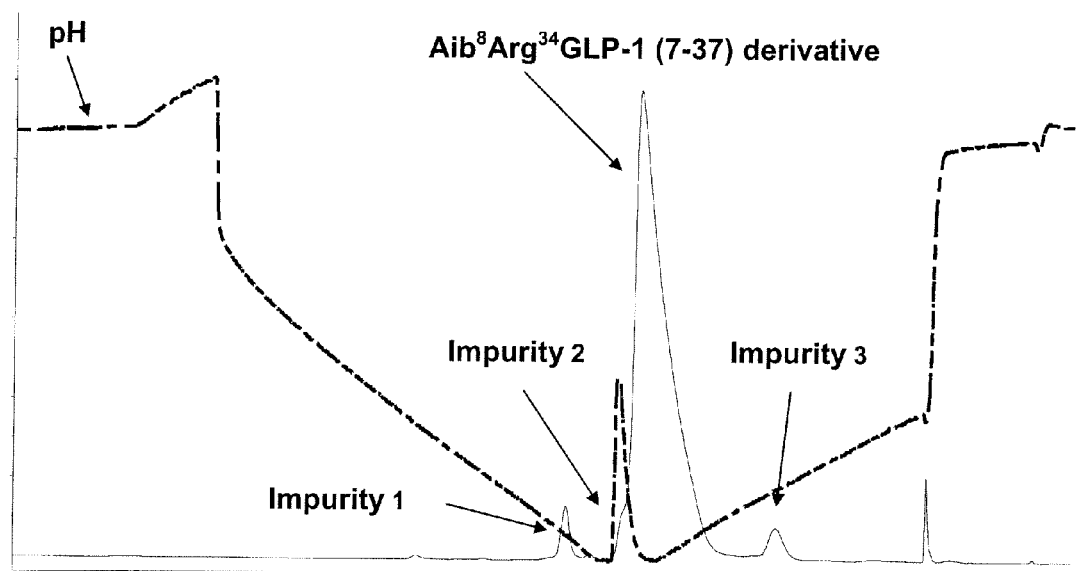
FIG. 5. Chromatogram of $AU_{280}$ versus time for the separation. Elution was performed first by a combination of pH (from neutral to pI or close to pI) and EtOH gradient (to just before the peptide of interest peak comes out), then a pH gradient from 4.5 to neutral.

A chromatogram of the preparative purification is shown in FIG. 5. From the chromatographic profile it can be observed that the impurity 2 is separated from the peptide of interest peak. The relative retention volume of impurity 2 to peptide of interest is about 0.96-0.97, a satisfied separation of impurity 2 and peptide of interest was obtained by pH gradient starts from pI value.

Example 5

RP HPLC Purification of Insulin Aspart

Human insulin aspart desB 30 was produced by ALP cleavage of human insulin aspart precursor, which was produced from yeast fermentation. 0.52 g crystals containing insulin aspart desB30 and related impurities were dissolved in 40 ml of 20 mmol/kg citrate buffer, 16% (w/w) ethanol, pH 4.0 and pH adjusted to about 3.7 to solublize the desB30. 20 ml of fluid mixture (11 mg/ml) was loaded onto a 20 ml $C_{18}$-substituted (octadecyl-dimethylsilyl) silica resin (particle size: 15 μm) equilibrated with about 60 ml of 20 mmol/kg citric acid buffer, 16% (w/w) ethanol, pH 4.0. The column was washed with 20 ml equilibration solution and elution was performed with a linear gradient of 16-29% (w/w) ethanol (20 mmol/kg citrate buffer, pH 5.8) for 200 ml, then isocratic wash at EtOH 29% (w/w) and pH 5.8 for 40 ml (20 mmol/kg citrate buffer, pH 5.8). The target human insulin desB30 was then eluted by a linear pH gradient elution from pH 5.8 to 8.0 (20 mmol/kg Tris buffer, EtOH 29% w/w, pH 8.0) for 200 ml. The chromatography was performed at room temperature.

Figure 6:
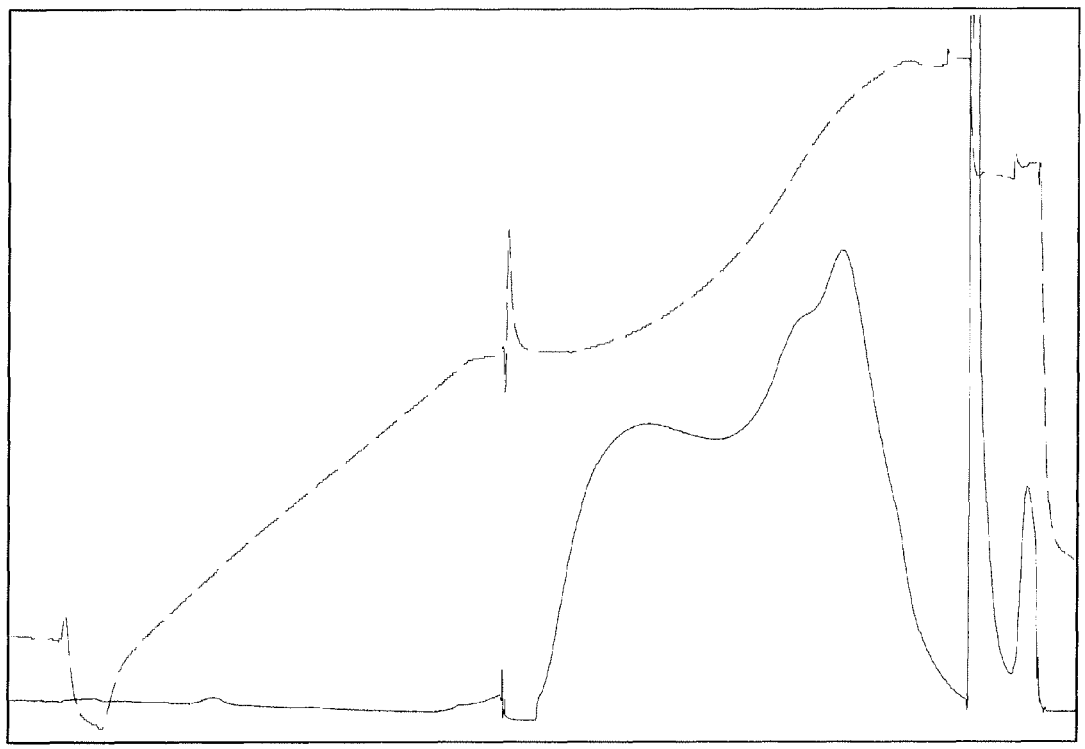
FIG. 6. DesB30 Human Insulin chromatogram of $AU_{280}$ versus time for the separation. Elution was performed first by a combination of pH (increasing from 4.0 to pI or close to pI) and EtOH gradient (to just before the peak with the peptide of interest comes out), followed by a stepwise elution at pI or pH close to pI, then a pH gradient from 5.8 to 8.0.

A chromatogram of the preparative purification is shown in FIG. 6. From the chromatographic profile it can be observed that an impurity peak is eluted out just before the peptide of interest peak.

Example 6

RP HPLC Purification of Palmitoyl-γ-Glu-Lys$^{26}$-Arg$^{34}$ GLP-1(7-37)Petide

Palmitoyl-γ-Glu-Lys$^{26}$-Arg$^{34}$ GLP-1(7-37) petide was produced from yeast fermentation. The acylated mixture containing Palmitoyl-γ-Glu-Lys$^{26}$-Arg$^{34}$ GLP-1(7-37) petide and related impurities was diluted by water. 36 ml of fluid mixture (4 mg/ml) was loaded onto a 20 ml $C_{18}$-substituted (octadecyl-dimethylsilyl) silica resin (particle size: 15 μm) equilibrated with about 60 ml of 20 mmol/kg Tris buffer, 20% (w/w) ethanol, pH 7.5. The column was washed with 20 ml equilibration solution and elution was performed with a linear gradient of 20-50% (w/w) ethanol (20 mmol/kg citrate buffer, pH 5.1) for 200 ml, then isocratic wash at EtOH 50% (w/w) and pH 5.1 for 40 ml (20 mmol/kg citrate buffer, pH 5.1). The target palmitoyl-γ-Glu-Lys$^{26}$-Arg$^{34}$ GLP-1(7-37) petide was then eluted by a linear pH gradient elution from pH 5.1 to 4.0 (20 mmol/kg citrate buffer, EtOH 50% w/w, pH 4.0) for 200 ml. The chromatographic temperature was kept at 60° C.

Figure 7:
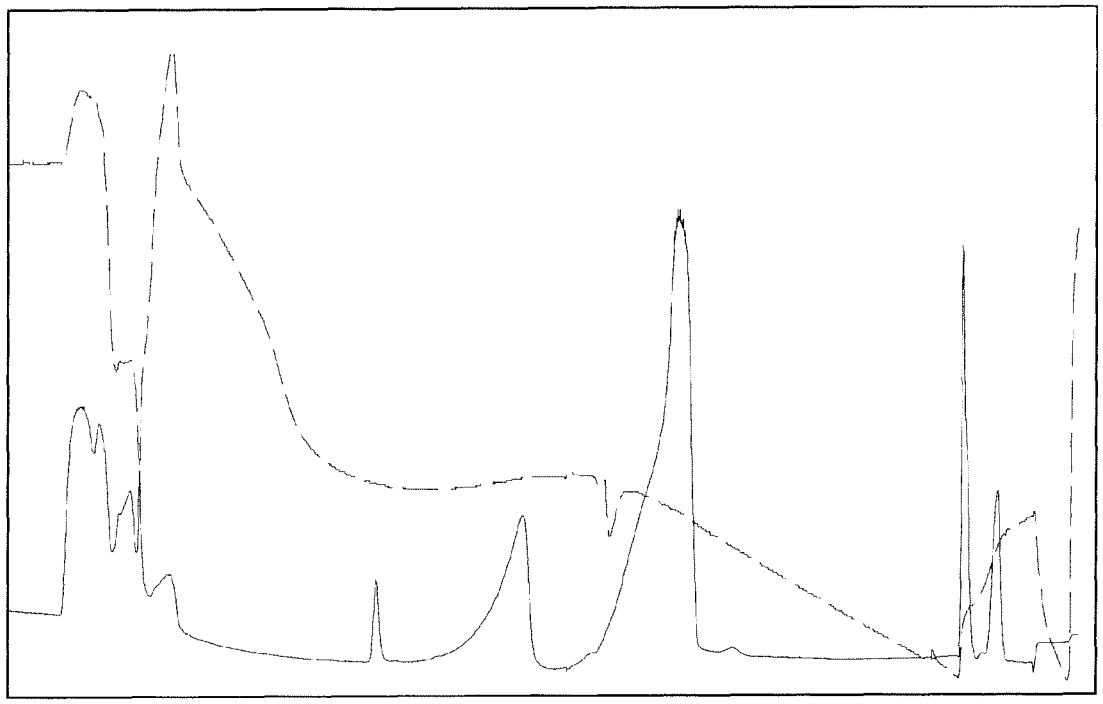
FIG. 7. $Arg^{34},Lys^{26}(N^{\epsilon}-(\gamma-Glu(N^{\alpha}-hexadecanoyl)))$-GLP-1(7-37)petide chromatogram of $AU_{280}$ versus time for the separation. Elution was performed first by a combination of pH (decreasing from pH 8.0 to pI or close to pI) and EtOH gradient (to just before the peptide of interest peak comes out), followed by a stepwise elution at pI or pH close to pI, then a pH gradient from 5.1 to 4.0.

A chromatogram of the preparative purification is shown in FIG. 7. From the chrometographic profile it can be observed that an impurity peak is separated from the peptide of interest peak.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

The invention claimed is:
1. A method of isolating a polypeptide of interest, the method comprising:
   a. introducing to a preparative reversed phase-high performance/pressure liquid chromatography (RP-HPLC) system a fluid mixture comprising the polypeptide of interest, the mixture being dissolved in a mobile phase, wherein the mobile phase has a pH value which is at least 1 unit from the pI value of the polypeptide of interest;

b. adjusting the pH of the mobile phase to a pH value which is less than 1 unit from the pI value of the polypeptide of interest, wherein the adjustment in pH is done in a step-wise procedure or with a pH gradient; and c. eluting the polypeptide of interest to provide a purified composition thereof;

wherein the polypeptide of interest is separated from at least one related impurity in the fluid mixture;

wherein said related impurity is selected from:
- a glycosylated form of,
- a deamidated form of,
- a truncated form of,
- an extended form of,
- an incorrectly folded form of,
- an oxidized form of,
- a form with undesired glycosylation of,
- a form resulting from racemization of,
- a form lacking amino acids in an intra-peptide chain of,
- a form having extra amino acids in an intra-peptide chain of, and
- a form wherein an acylation has taken place on another residue than desired of, the polypeptide of interest; and wherein the polypeptide of interest is a Glucagon-Like Peptide-1 (GLP-1) selected from N-$\epsilon^{26}$-[2-(-2-[2-(2-[2-(2-[4-(17-Carboxyheptadecanoylamino)-4(s)-carboxybutyrylaminol]ethoxy)ethoxyl]acetylamino)ethoxyl]ethoxy)acetyl]-Aib8,Arg34-GLP-1(7-37); and Arg$^{34}$, Lys$^{26}$(N$^{\epsilon}$-($\gamma$-Glu(N$^{\alpha}$-hexadecanoyl)))-GLP-1(7-37).

2. The method according to claim 1, wherein a step is added between step b and step c, wherein pH is again adjusted to a pH value which is at least 1 unit from the pI value of the peptide or protein to be purified, and wherein said adjustment is done in a step-wise procedure or with a pH gradient.

3. The method according to claim 1, wherein the pH value in step a is higher than the pI value of the polypeptide of interest.

4. The method according to claim 1, wherein the pH value in step a is between 5.5 and 9.0.

5. The method according to claim 1, wherein the pH value in step b is between 3.5 and 5.5.

6. The method according to claim 1, wherein adjusting the pH of the mobile phase in step b is with a pH gradient.

7. The method according to claim 1, wherein the method comprises applying a gradient of an organic modifier simultaneously with step b to remove the at least one related impurity while retaining the polypeptide of interest on the RP-HPLC system, and wherein the organic modifier is selected from the group consisting of ethanol, methanol, propanol, and acetonitrile.

8. The method according to claim 7, wherein the gradient of the organic modifier in step b is from about 25% to about 48% and adjusting the pH of the mobile phase is with a pH gradient from pH 7.4 to 4.5.

9. The method according to claim 1, wherein adjusting the pH of the mobile phase in step b is from about 7.4 to about 4.5.

10. The method according to claim 1, wherein the temperature on the RP-HPLC system is between 20 and 70 degrees Celsius.

11. The method according to claim 1, wherein the RP-HPLC system uses an adsorbent comprising a substituted silica selected from the group consisting of C-4 silica, C-6 silica, C-8 silica, C-12 silica, C-16 silica, C-18 silica, C-20 silica, and phenyl-based silica.

12. The method according to claim 1, wherein the polypeptide of interest is a polypeptide suitable for treating diabetes.

13. The method according to claim 12, wherein the polypeptide of interest is a glucagon-like peptide or a GLP-1 agonist.

14. The method according to claim 1, wherein the at least one related impurity is another form of the polypeptide of interest, the another form of the polypeptide of interest is selected from the group consisting of a glycosylated form of the polypeptide of interest, a deamidated form of the polypeptide of interest, and an oxidized form of the polypeptide of interest.

* * * * *